US010646853B2

(12) United States Patent
Fridman

(10) Patent No.: US 10,646,853 B2
(45) Date of Patent: May 12, 2020

(54) CHROMIUM CATALYST MATERIALS AND METHODS FOR MAKING AND USING THE SAME FROM CHROMIUM(VI) FREE SOURCES

(71) Applicant: Clariant Corporation, Louisville, KY (US)

(72) Inventor: Vladimir Fridman, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 15/865,517

(22) Filed: Jan. 9, 2018

(65) Prior Publication Data

US 2018/0214852 A1 Aug. 2, 2018

Related U.S. Application Data

(60) Provisional application No. 62/453,590, filed on Feb. 2, 2017.

(51) Int. Cl.
| | | |
|---|---|---|
| *B01J 23/26* | (2006.01) | |
| *B01J 37/02* | (2006.01) | |
| *B01J 37/08* | (2006.01) | |
| *C07C 5/03* | (2006.01) | |
| *B01J 37/00* | (2006.01) | |
| *B01J 37/04* | (2006.01) | |
| *B01J 21/04* | (2006.01) | |

(52) U.S. Cl.
CPC .............. *B01J 23/26* (2013.01); *B01J 21/04* (2013.01); *B01J 37/0009* (2013.01); *B01J 37/0018* (2013.01); *B01J 37/0201* (2013.01); *B01J 37/0236* (2013.01); *B01J 37/04* (2013.01); *B01J 37/08* (2013.01); *B01J 37/088* (2013.01); *C07C 5/03* (2013.01); *C07C 2521/04* (2013.01); *C07C 2523/26* (2013.01)

(58) Field of Classification Search
CPC ... B01J 21/04; B01J 21/08; B01J 23/26; B01J 37/0018; B01J 37/0201; B01J 37/04; B01J 37/08
See application file for complete search history.

(56) References Cited

U.S. PATENT DOCUMENTS

| | | | |
|---|---|---|---|
| 2,375,402 A | 5/1945 | Corson | |
| 5,378,350 A | 1/1995 | Zimmermann | |
| 6,084,145 A * | 7/2000 | Wu .......................... | B01J 23/26 |
| | | | 502/64 |
| 8,101,541 B2 | 1/2012 | Fridman | |
| 8,835,347 B2 | 9/2014 | Ruettinger | |
| 8,895,468 B2 | 11/2014 | Ruettinger | |
| 2003/0232720 A1* | 12/2003 | Alerasool ................ | B01J 23/26 |
| | | | 502/317 |
| 2005/0075243 A1 | 4/2005 | Fridman | |
| 2013/0072739 A1* | 3/2013 | Ruettinger ............... | B01J 21/12 |
| | | | 585/662 |

FOREIGN PATENT DOCUMENTS

WO 2014096628 6/2014

OTHER PUBLICATIONS

Rubinstein, A.M., "Phase composition and the texture of aluminochromium catalysts prepared by simultaneous precipitation" (Bulletin of the Academy of Sciences of the USSR, Division of Chemical Science, 780-8 (1961).

Weckhuysen, Bert M. "Alkane dehydrogenation over supported chromium oxide catalysts" Catalysis Today 51 (1999) 223-232.

\* cited by examiner

*Primary Examiner* — Jun Li

(57) ABSTRACT

The present disclosure relates to methods for making chromium-containing dehydrogenation catalysts using chromium feedstocks that need not include chromium(VI). The disclosure also relates to the catalysts made thereby, as well as to dehydrogenation methods using such catalysts. In one aspect of the disclosure, a method includes providing a formable mixture comprising, on a dry basis, an aluminum hydroxide, present in an amount within the range of about 40 wt. % to about 90 wt. %; an acid (e.g., nitric acid), present in an amount within the range of about 2 wt. % to about 15 wt. %; and a chromium(III) source, present in an amount within the range of about 2 wt. % to about 35 wt. %; forming the formable mixture; and calcining the formed mixture. In certain embodiments, the method further includes impregnating the calcined mixture with an aqueous impregnation solution including a chromium(III) salt; and calcining the impregnated mixture.

16 Claims, No Drawings

CHROMIUM CATALYST MATERIALS AND METHODS FOR MAKING AND USING THE SAME FROM CHROMIUM(VI) FREE SOURCES

CROSS-REFERENCE TO RELATED APPLICATIONS

This application claims the benefit of priority of U.S. Provisional Patent Application No. 62/453,590, filed Feb. 2, 2017, which is hereby incorporated herein by reference in its entirety.

BACKGROUND OF THE DISCLOSURE

Field of the Disclosure

This disclosure relates generally to catalyst materials. More particularly, the present disclosure relates to chromium-containing catalysts useful in the dehydrogenation of hydrocarbons, to methods for making such catalysts, and to methods for dehydrogenating hydrocarbons comprising contacting hydrocarbons with such catalyst.

Technical Background

Alkane dehydrogenation is a recognized process for production of a variety of useful hydrocarbon products, such as isobutylene for conversion to methyl tert-butyl ether, isooctane and alkylates to supplement and enrich gasolines and propylene for use in the polymer industry. Current catalysts useful for catalytic dehydrogenation of light alkanes utilize either chromium-aluminum catalysts, or precious metal(s) on support catalysts.

Current chromium-aluminum dehydrogenation catalysts are produced through a one-step impregnation of an aluminum carrier with high-concentration chromic acid solution, which contains primarily hexavalent chromium (chromium (VI) or Cr(VI)), which is toxic and carcinogenic, and therefore highly undesirable for use on an industrial scale.

Current methods for the production of chromium-aluminum dehydrogenation catalysts without the use of chromium (VI)-containing materials are limited. One such method is the precipitation of aluminum nitrate and chromium nitrate by ammonia solution, followed by washing and calcination of the precipitate. However, Rubinstein et al. (Bulletin of the Academy of Sciences of the USSR, Division of Chemical Science, 780-8 (1961)) showed that the resulting material contained the kappa phase of aluminum oxide, which strongly negatively affects catalyst stability.

Accordingly, there remains a need for a simple, cost-effective method for making an aluminum-chromium dehydrogenation catalyst without chromium(VI)-containing materials.

SUMMARY OF THE DISCLOSURE

One aspect of the disclosure is a method for preparing a chromium catalyst, the method comprising
  providing a formable mixture comprising, on a dry basis,
    an aluminum hydroxide, present in an amount within the range of about 40 wt. % to about 90 wt. %;
    an acid (e.g., nitric acid), present in an amount within the range of about 2 wt. % to about 15 wt. %; and
    a chromium(III) source, present in an amount within the range of about 2 wt. % to about 35 wt. %;
  forming the formable mixture; and
  calcining the formed mixture.

Another aspect of the disclosure is a method as described above, further including impregnating the calcined mixture with an aqueous impregnation solution that includes a chromium(III) salt; and calcining the impregnated mixture.

Another aspect of the disclosure is a dehydrogenation catalyst prepared by a method as described herein.

Another aspect of the disclosure is a method for dehydrogenating hydrocarbons, the method including contacting a hydrocarbon feed with a dehydrogenation catalyst as described herein.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

In various aspects and embodiments, the disclosure relates to chromium catalyst materials prepared by forming and calcining a formable mixture comprising an aluminum hydroxide, an acid such as nitric acid, and a chromium(III) source such as a chromium(III) oxide. The disclosure demonstrates the preparation of such dehydrogenation catalysts in the absence of chromium(VI)-containing materials, without negatively impacting final dehydrogenation catalyst performance relative to catalysts prepared according to conventional methods.

The present inventors have noted that a method involving impregnation of an aluminum carrier with a chromium(III) salt required multiple impregnation steps to arrive at a desirable chromium content. Each impregnation step would require intermediate drying and calcination, and so such a multi-impregnation method would be time- and labor-intensive, and cost prohibitive relative to conventional preparation procedures involving chromium(VI)-containing materials.

One aspect of the disclosure is a method of preparing a chromium catalyst suitable, for example, for industrial-scale dehydrogenation reactions. The method includes providing a formable mixture comprising an aluminum hydroxide present in an amount within the range of about 40 wt. % to about 90 wt. % on a dry basis, an acid (such as nitric acid) present in an amount within the range of about 2 wt. % to about 15 wt. % on a dry basis, and a chromium(III) source (such as chromium(III) oxide ($Cr_2O_3$)) present in an amount within the range of about 2 wt. % to about 35 wt. % on a dry basis. The formable mixture can include sufficient water to make the mixture formable (i.e., by any desired process including extrusion, tabletting and pelletization). The method includes forming the formable mixture and calcining the formed mixture.

The amounts of the components in the formable mixture can be described herein on a "dry basis," i.e., exclusive of any water present. The person of ordinary skill in the art will appreciate that there will be sufficient water present to make the mixture formable. When the amount a component of a material is described on a "wet basis", it is described as a percentage of the total mass of the formable mixture.

As noted above, the formable mixture includes an aluminum hydroxide. In certain embodiments of the methods as otherwise described herein, the aluminum hydroxide can be, for example, a material with a significant aluminum hydroxide content, i.e., any material of the formula $Al(OH)_X(O)_{1-X}$, wherein X is at least 0.3. For example, in some embodiments of the methods as otherwise described herein, the aluminum hydroxide is an aluminum trihydroxide, e.g., bayerite, gibbsite, doyleite, or nordstrandite. In other embodiments of the methods as otherwise described herein, the aluminum hydroxide is aluminum oxide hydroxide, e.g., diaspore, boehmite, psuedoboehmite, or akdalaite. The person of ordinary skill in the art would appreciate that the aluminum hydroxide can include small amounts of impurities as is conventional for industrial-grade materials.

As noted above, the formable mixture includes the aluminum hydroxide in an amount within the range of about 40 wt. % to about 90 wt. % on a dry basis. For example, in some embodiments of the methods as otherwise described herein, the formable mixture includes an aluminum hydroxide present in an amount within the range of 60 wt. % to about 90 wt. %, or about 40 wt. % to about 90 wt. %, or about 40 wt. % to about 80 wt. %, or about 50 wt. % to about 90 wt. %, or about 50 wt. % to about 80 wt. %, or about 60 wt. % to about 80 wt. %, or about 40 wt. % to about 70 wt. %, or about 50 wt. % to about 70 wt. %, all on a dry basis.

Also noted above, the formable mixture includes an acid. In certain embodiments of the process as otherwise described herein, the acid is nitric acid. In other embodiments of the process as otherwise described herein, the acid is an organic acid, such as formic acid or acetic acid. In still other embodiments of the process as otherwise described herein, the acid is a combination of nitric acid and an organic acid such as formic acid or acetic acid. The use of an organic acid can be beneficial in that it can reduce the $NO_x$ concentration during heat treatment; however, it can also make the peptization of alumina less efficient. The person of ordinary skill in the art will determine the appropriate amounts and types of acids to use to provide a desired material.

As noted above, the formable mixture includes an acid (e.g., nitric acid) in an amount within the range of about 2 wt. % to about 15 wt. % on a dry basis. In certain embodiments of the methods as otherwise described herein, the acid (e.g., nitric acid) is present in the formable mixture in an amount within the range of about 2 wt. % to about 12 wt. %, or about, 2 wt. % to about 10 wt. %, or about 2 wt. % to about 8 wt. %, or about 4 wt. % to about 15 wt. %, or about 4 wt. % to about 10 wt. %, or about 4 wt. % to about 8 wt. %, or about 6 wt. % to about 15 wt. %, or about 6 wt. % to about 10 wt. %, all on a dry basis.

As the person of ordinary skill in the art will appreciate, the acid can be provided to the mixture in any convenient form. For example, the acid may be provided to the mixture in concentrated form (e.g., for nitric acid, 68-70% by weight, or even up to about 90% by weight). The acid may alternatively be provided to the mixture as an aqueous solution of a lower concentration. But as the weight percent of acid is calculated herein on a dry basis, the amounts specified for use in the formable mixtures described herein are quantified with respect to pure acid, i.e., for nitric acid, 100% $HNO_3$.

As noted above, the formable mixture includes a chromium(III) source. In certain embodiments of the methods as otherwise described herein, the chromium(III) source can be, for example, chromium(III) oxide. A suitable source for chromium(III) oxide is the ACCROX materials available from Elementis Chromium. In other embodiments of the methods as otherwise described herein, the chromium(III) source is chromium(III) hydroxide, chromium(III) halide, chromium(III) acetate or chromium(III) stearate. The person of ordinary skill in the art will appreciate that other chromium(III) sources may be used; however, chromium(III) sulfate is generally undesirable for use in the presently described processes.

As noted above, the formable mixture includes the chromium(III) source (e.g., chromium(III) oxide) in an amount within the range of about 2 wt. % to about 35 wt. % on a dry basis. For example, in some embodiments of the methods as otherwise described herein, the formable mixture includes the chromium(III) source (e.g., chromium (III) oxide) in an amount within the range of about 3 wt. % to about 35 wt. %, or about 5 wt. % to about 35 wt. %, or about 10 wt. % to about 35 wt. %, or about 2 wt. % to about 30 wt. %, or about 3 wt. % to about 30 wt. %, or about 5 wt. % to about 30 wt. %, or about 10 wt. % to about 30 wt. %, or about 2 wt. % to about 25 wt. %, or about 3 wt. % to about 25 wt. %, or about 5 wt. % to about 25 wt. %, or about 10 wt. % to about 25 wt. %, or about 2 wt. % to about 20 wt. %, or about 3 wt. % to about 20 wt. %, or about 5 wt. % to about 20 wt. %, or about 10 wt. % to about 20 wt. %, all on a dry basis.

The amounts of chromium source and aluminum hydroxide in the formable mixture can also be defined on an as-calcined basis, i.e., based on the amount of chromium oxide (as $Cr_2O_3$) and aluminum oxide (as $Al_2O_3$) in the calcined product of the formable mixture. For example, in certain embodiments of the methods as otherwise described herein, the amount of the chromium(III) source in the formable mixture is in the range of about 5 wt. % to about 35 wt. % on a calcined basis as $Cr_2O_3$. In various embodiments of the methods as otherwise described herein, the amount of the chromium(III) source in the formable mixture is in the range of about 10 wt. % to about 35 wt. %, or about 15 wt. % to about 35 wt. %, or about 5 wt. % to about 30 wt. %, or about 10 wt. % to about 30 wt. %, or about 15 wt. % to about 30 wt. %, or about 5 wt. % to about 25 wt. %, or about 10 wt. % to about 25 wt. %, or about 15 wt. % to about 25 wt. %, all on a calcined basis as $Cr_2O_3$.

Similarly, in certain embodiments of the methods as otherwise described herein, the amount of the aluminum hydroxide in the formable mixture is in the range of about 65 wt. % to about 95 wt. % on a calcined basis as $Al_2O_3$. In various embodiments of the methods as otherwise described herein, the amount of the aluminum hydroxide in the formable mixture is in the range of about 70 wt. % to about 95 wt. %, or about 75 wt. % to about 95 wt. %, or about 65 wt. % to about 90 wt. %, or about 70 wt. % to about 90 wt. %, or about 75 wt. % to about 90 wt. %, or about 65 wt. % to about 85 wt. %, or about 70 wt. % to about 85 wt. %, or about 75 wt. % to about 85 wt. %, all on a calcined basis as $Al_2O_3$.

The person of ordinary skill in the art will appreciate that the formable mixture will contain water in an amount that allows the mixture to be formable, e.g., extruded, tableted or pelletized. The amount of water can be, for example, about 3 wt. % to about 20 wt. % on a wet basis. In certain embodiments, the amount of water is, for example, about 5 wt. % to about 20 wt. %, or about 8 wt. % to about 20 wt. %, or about 10 wt. % to about 20 wt. %, or about 3 wt. % to about 15 wt. %, or about 5 wt. % to about 15 wt. %, or about 8 wt. % to about 15 wt. %, or about 10 wt. % to about 15 wt. %, or about 3 wt. % to about 10 wt. %, or about 5 wt. % to about 10 wt. %, all on a wet basis.

Below are described additional metallic components (i.e., sodium, magnesium, potassium, zirconium) that can be added via impregnation. These components can alternatively or additionally be added via the formable mixture, using appropriate sources. The total amount of such components in the dehydrogenation catalyst can be as described below.

The formable mixture can, of course, include other conventional materials such as binders, cements, pore formers, texturizers, extrusion aids, lubricants, surfactants, and any other materials to aid with mixing or forming, or to provide a desired structure to the as-calcined material. For example, in certain embodiments, the formable mixture includes a pore forming organic compound, such as a polymer. The pore forming organic compound does not dissolve into the water of the formable mixture, and thus remains as discrete small regions of organic matter within the material when formed. During the calcination, the pore forming organic compound is burned away, which forms a gas that increases the porosity of the calcined material. The pore forming organic polymer can be, for example, a polyolefin such as polyethylene, or a cellulose derivative such as methocel. The pore forming organic compound can be provided in the formable mixture in any desirable amount, for example, in an amount within the range of about 0.1 wt. % to about 5 wt. % on a dry basis. In certain embodiments, the pore forming organic compound is present in the formable mixture in an amount within the range of about 0.2 wt. % to about 5 wt. %, or about 0.5 wt. % to about 5 wt. %, or about 0.1 wt. % to about 3 wt. %, or about 0.2 wt. % to about 3 wt. %, or about 0.5 wt. % to about 3 wt. %, or about 0.1 wt. % to about 2 wt. %, or about 0.2 wt. % to about 2 wt. %, or about 0.5 wt. % to about 2 wt. %.

While the person of ordinary skill in the art will appreciate that a number of other components can be present in the formable mixture, in certain desirable embodiments the aluminum hydroxide, the acid and the chromium(III) source make up the bulk of the dry mass of the formable mixture. For example, in certain embodiments of the methods as described herein, the aluminum hydroxide, the acid and the chromium(III) source make up at least about 80 wt. % of the formable mixture on a dry basis. In certain particular embodiments of the methods as described herein, the aluminum hydroxide, the acid and the chromium source make up at least about 90 wt. %, at least about 95 wt. %, or at least about 98 wt. % of the formable mixture on a dry basis.

The person of ordinary skill in the art will appreciate that the various components can be mixed by a variety of methods, both manual and mechanical, to provide the formable mixture. For example, in certain embodiments, the formable mixture is mixed by a batch mixer. But other batch or continuous processes can be used to create the formable mixture. Components may be added serially or together in any convenient order, as would be apparent to the person of ordinary skill in the art.

As described above, the method of preparing the chromium catalyst includes forming the formable mixture. The person of ordinary skill in the art will appreciate that the formable mixture may be formed into a variety of shapes, e.g., pellets, tablets, spheres, tablets, cylinders, stars, tri-lobes, quadra-lobes, pills, granules, honeycombs, and cubes. A variety of forming methods are known in the art, e.g., extrusion, pelletizing, tableting, granulation, marumarizing. In certain embodiments, the formable mixture is formed into pellets, e.g., by direct pelletizing or by extrusion into strands that are cut into pellets. The person of ordinary skill in the art will appreciate that the shape and dimensions of the formed mixture will depend on the methods used to form the mixture and on the desired end process. The person of ordinary skill in the art will appreciate that the formable mixture may be provided and formed without including any materials comprising chromium(VI). In certain embodiments of the methods as described herein, the formed mixture before the calcining step includes less than 1.0% chromium(VI), e.g., less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, or less than 0.001%, calculated on a molar basis based on the total amount of chromium. This can be accomplished, for example, through the use of a chromium(III) source that includes less than 1.0% chromium(VI), e.g., less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or even less than 0.01%, or less than 0.001%, calculated on a molar basis based on the total amount of chromium.

The method of preparing the chromium catalyst also includes calcining the formed mixture. In some embodiments, the formed mixture is calcined at a temperature within the range of about 300° C. to about 900° C., e.g., about 350° C. to about 850° C., or about 400° C. to about 800° C., or about 450° C. to about 750° C., or about 500° C. to about 700° C., or about 525° C. to about 675° C., or about 550° C. to about 650° C., or about 575° C. to about 625° C., or the temperature is about 350° C., or about 400° C., or about 450° C., or about 500° C., or about 525° C., or about 550° C., or about 575° C., or about 600° C., or about 625° C., or about 650° C., or about 675° C., or about 700° C., or about 750° C., or about 800° C., or about 850° C.

In some embodiments, the formed mixture is calcined for a period of time within the range of about 1 hr. to about 20 hr., e.g., about 2 hr. to about 12 hr. But the person of ordinary skill in the art can determine a desired calcination time. The calcination can be performed, for example, in air, or in any other suitable oxygen-containing atmosphere.

The person of ordinary skill in the art will select calcination conditions, including, possibly, time, temperatures, oxygen levels and moisture levels, and including multiple calcination steps at different conditions, to provide the desired material.

The formed mixture may be calcined in two or more stages, with each stage having its own time, temperature, oxygen level, and moisture level. For example, the extrudates may be dried at 120° C. for 1 hour in dry air, calcined at 400° C. for 1.5 hours in dry air, and then steamed at 200° C. for 0.5 hours in a 4:1 mixture of air and steam. However, it is not necessary to employ multiple calcination stages: a single stage in which the formed mixture is held at a constant temperature for a certain amount of time may also be used.

In certain embodiments of the methods as otherwise described herein, the major dimension of the calcined mixture, i.e., the diameter of a spherical shape, the longer of the length or diameter of a cylindrical shape, or the length of a rectangular cuboid shape, etc., taken as an average over the individual pieces of the material, is within the range of about 500 μm to about 5 cm, e.g., about 500 μm to about 4 cm, or about 500 μm to about 3 cm, or about 500 μm to about 2 cm, or about 750 μm to about 1.5 cm, or about 1 mm to about 1 cm, or about 1 mm to about 750 mm, or about 1 mm to about 500 mm, or about 1 mm to about 250 mm, or about 1 mm to about 200 mm, or about 1 mm to about 150 mm, or about 1 mm to about 100 mm, or about 1 mm to about 75 mm, or about 1 mm to about 50 mm, or about 1 mm to about 25 mm, or about 1 mm to about 20 mm, or about 1 mm to about 15 mm, or about 1 mm to about 10 mm, or about 1 mm to about 5 mm, or the dimension is about 500 μm, or about 750 μm, or about 1 mm, or about 1.5 mm, or about 2 mm, or about 2.5 mm, or about 3 mm, or about 3.5 mm, or about 4 mm, or about 4.5 mm, or about 5 mm, or about 10 mm, or about 25 mm, or about 50 mm, or about 75 mm, or about 100 mm, or about 250 mm, or about 500 mm, or about 750 mm, or about 1 cm.

The calcined mixture described above can in certain embodiments itself be useful as a catalyst. Nonetheless, in other embodiments it can be desirable to increase the amount of chromium in the mixture to arrive at a dehydrogenation catalyst. Thus, in certain embodiments of the methods as otherwise described herein, the method of preparing the chromium catalyst further includes impregnating the calcined mixture with an aqueous impregnation solution comprising a chromium(III) salt, then calcining the impregnated mixture. In some embodiments, the chromium(III) salt is chromium(III) nitrate, which is especially desirable due to its relatively high solubility in water. In other embodiments, the chromium(III)_salt is the salt of an organic acid, such as chromium(III) acetate; these often require multiple impregnation steps as a result of their lower solubilities. In various embodiments of the impregnation methods as otherwise described herein, the chromium(III) salt is present in the aqueous solution in an amount within the range of about 20 wt. % to about 50 wt. %, e.g., about 22.5 wt. % to about 50 wt. %, or about 25 wt. % to about 50 wt. %, or about 27.5 wt. % to about 47.5 wt. %, or about 30 wt. % to about 45 wt. %, or about 32.5 wt. % to about 42.5 wt. %, or about 35 wt. % to about 40 wt. %, or the amount is about 25 wt. %, or about 27.5 wt. %, or about 30 wt. %, or about 32.5 wt. %, or about 35 wt. %, or about 37.5 wt. %, or about 40 wt. %, or about 42.5 wt. %, or about 45 wt. %. In certain embodiments, the chromium(III) salt is present in the impregnation solution in an amount sufficient to provide a final catalyst material having a chromium content in the range of about 15 wt. % to about 50 wt. %, as $Cr_2O_3$ on a calcined basis. In various embodiments, the chromium(III) salt is present in the impregnation solution in an amount sufficient to provide the final catalyst material having a chromium content in the range of about 20 wt. % to about 50 wt. %, or about 25 wt. % to about 50 wt. %, or about 30 wt. % to about 50 wt. %, or about 15 wt. % to about 45 wt. %, or about 20 wt. % to about 45 wt. %, or about 25 wt. % to about 45 wt. %, or about 30 wt. % to about 45 wt. %, or about 15 wt. % to about 40 wt. %, or about 20 wt. % to about 40 wt. %, or about 25 wt. % to about 40 wt. %, or about 30 wt. % to about 40 wt. %, all as $Cr_2O_3$ on a calcined basis.

As the person of ordinary skill will appreciate, the impregnation will increase the amount of chromium in the material. In certain embodiments of the methods described herein, the impregnation increases the amount of chromium in the material on a dry basis (i.e., comparing the amount of chromium in the calcined material to the amount of chromium in the dehydrogenation catalyst, calculated as $Cr_2O_3$ on a calcined basis) by about 2 wt. % to about 15 wt. %.

In some embodiments of the methods as otherwise described herein, the aqueous impregnation solution further comprises an alkali metal salt. The alkali metal ion can help suppress the acidity of the aluminum oxide and improve selectivity of the catalyst. For example, in some embodiments of the methods as otherwise described herein, the alkali metal salt is a sodium salt. In other embodiments, the alkali metal salt is a lithium salt or a potassium salt. The person of ordinary skill in the art will appreciate that the alkali metal salt can be provided with a variety of counterions. For example, in certain embodiments, the alkali metal salt is provided as a hydroxide. In other embodiments, the alkali metal salt is provided as a carbonate, or an acetate. Nitrates can be used, but will create additional NOR. Halides and sulfates are generally undesirable for use. In certain embodiments of the methods as otherwise described herein, the alkali metal salt is present in the impregnation solution in a concentration sufficient to provide the final catalyst material with the alkali metal in an amount within the range of about 0.1 wt. % to about 5 wt. %, e.g., about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, calculated as alkali metal oxide on a calcined basis.

In some embodiments of the methods as otherwise described herein, the aqueous impregnation solution further comprises a zirconium salt. Zirconium can beneficially act as a stabilizer in the final catalyst material. For example, in some embodiments of the methods as otherwise described herein, the zirconium salt is zirconium carbonate. In other embodiments, the zirconium salt is zirconium oxynitrate, however its use can increase the amount of NOx. In certain embodiments of the methods as otherwise described herein, the zirconium salt is present in the impregnation solution in a concentration sufficient to provide the final catalyst material with the zirconium in an amount within the range of about 0.1 wt. % to about 5 wt. %, e.g., about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, as $ZrO_2$ on a calcined basis.

In some embodiments of the methods as otherwise described herein, the aqueous impregnation solution further comprises a magnesium salt. For example, in some embodiments of the methods as otherwise described herein, the magnesium salt is magnesium hydroxide. In certain embodiments of the methods as otherwise described herein, the magnesium salt is present in the impregnation solution in a concentration sufficient to provide the final catalyst material with the magnesium in an amount within the range of about 0.1 wt. % to about 5 wt. %, e.g., about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, as MgO on a calcined basis.

In one embodiment, the aqueous impregnation solution comprises a sodium salt, e.g., sodium hydroxide, present in an amount sufficient to provide the catalyst with sodium within the range of about 0.1 wt. % to about 5 wt. % (or any other amount detailed above) calculated as sodium oxide on a calcined basis; and a zirconium salt, e.g., zirconium carbonate, present in an amount sufficient to provide the catalyst with zirconium within the range of about 0.1 wt. % to about 5 wt. % (or any other amount detailed above) calculated as $ZrO_2$ on a calcined basis. In another embodiment, the aqueous impregnation solution comprises a sodium salt, e.g., sodium hydroxide, present in an amount sufficient to provide the catalyst with sodium within the range of about 0.1 wt. % to about 5 wt. % (or any other amount detailed above) calculated as sodium oxide on a calcined basis; and a potassium salt, e.g., potassium hydroxide, present in an amount sufficient to provide the catalyst with potassium within the range of about 0.1 wt. % to about 5 wt. % (or any other amount detailed above) calculated as potassium oxide on a calcined basis. In yet another embodiment, the aqueous impregnation solution comprises an alkali metal salt, e.g., sodium hydroxide, sodium nitrate, potassium nitrate or potassium hydroxide, present in an amount sufficient to provide the catalyst with alkali metal within the range of about 0.1 wt. % to about 5 wt. % (or any other amount detailed above) calculated as alkali metal oxide on a calcined basis; and a zirconium salt, e.g., zirconium carbonate, present in an amount sufficient to provide the catalyst with zirconium within the range of about 0.1 wt. % to about 5 wt. % (or any other amount detailed above), calculated as $ZrO_2$ on a calcined basis. In yet another embodiment, the aqueous impregnation solution comprises an alkali metal salt, e.g., sodium hydroxide sodium nitrate, potassium nitrate or potassium hydroxide, present in an amount sufficient to provide the catalyst with alkali metal within the range of about 0.1 wt. % to about 5 wt. % (or any other amount detailed above) calculated as alkali metal oxide on a calcined basis; and a magnesium salt, e.g., magnesium hydroxide or magnesium nitrate, present in an amount sufficient to provide the catalyst with magnesium within the range of about 0.1 wt. % to about 5 wt. % (or any other amount detailed above) calculated as MgO on a calcined basis. In another embodiment, the aqueous impregnation solution comprises a zirconium salt, e.g., zirconium carbonate or zirconium oxynitrate, present in an amount sufficient to provide the catalyst with zirconium within the range of about 0.1 wt. % to about 5 wt. % (or any other amount detailed above), calculated as $ZrO_2$ on a calcined basis; and a magnesium salt, e.g., magnesium hydroxide or magnesium nitrate, present in an amount sufficient to provide the catalyst with magnesium within the range of about 0.1 wt. % to about 5 wt. % (or any other amount detailed above) calculated as MgO on a calcined basis.

Notably, like the extrusion/calcination to form the calcined mixture, the impregnation process can be performed in the substantial absence of chromium(VI). Accordingly, in some embodiments of the methods as otherwise described herein, the materials included in the aqueous impregnation solution comprise chromium(VI) in an amount of less than 1%, e.g., less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, or less than 0.001%, calculated on a molar basis based on the total amount of chromium.

Following impregnation, the impregnated mixture is calcined. In some embodiments of the methods as otherwise described herein, the impregnated mixture is calcined at a temperature within the range of about 400° C. to about 1000° C., e.g., about 425° C. to about 1000° C., or about 450° C. to about 1000° C., or about 475° C. to about 1000° C., or about 500° C. to about 1000° C., or about 525° C. to about 975° C., or about 550° C. to about 950° C., or about 575° C. to about 925° C., or about 600° C. to about 900° C., or about 625° C. to about 875° C., or about 650° C. to about 850° C., or about 675° C. to about 825° C., or about 700° C. to about 800° C., or the temperature is about 500° C., or about 525° C., or about 550° C., or about 575° C., or about 600° C., or about 625° C., or about 650° C., or about 675° C., or about 700° C., or about 725° C., or about 750° C., or about 775° C., or about 800° C., or about 825° C., or about 850° C., or about 875° C., or about 900° C.

Another aspect of the disclosure is a dehydrogenation catalyst made by any method as described herein. In certain embodiments, the surface area of the dehydrogenation catalyst as otherwise described herein is at least about 125 $m^2/g$, e.g., at least about 130 $m^2/g$, or at least about 135 $m^2/g$, or at least about 140 $m^2/g$, or at least about 145 $m^2/g$, or at least about 150 $m^2/g$, or at least about 155 $m^2/g$, or at least about 160 $m^2/g$, or at least about 165 $m^2/g$, or at least about 170 $m^2/g$, or at least about 175 $m^2/g$.

In some embodiments of the dehydrogenation catalysts as otherwise described herein, chromium is present in the dehydrogenation catalyst in an amount within the range of about 15 wt. % to about 50 wt. %, calculated as $Cr_2O_3$ on a calcined basis. In various embodiments, the dehydrogenation catalyst has a chromium content in the range of about 20 wt. % to about 50 wt. %, or about 25 wt. % to about 50 wt. %, or about 30 wt. % to about 50 wt. %, or about 15 wt. % to about 45 wt. %, or about 20 wt. % to about 45 wt. %, or about 25 wt. % to about 45 wt. %, or about 30 wt. % to about 45 wt. %, or about 15 wt. % to about 40 wt. %, or about 20 wt. % to about 40 wt. %, or about 25 wt. % to about 40 wt. %, or about 30 wt. % to about 40 wt. %, or about 15 wt. % to about 37.5 wt. %, or about 15 wt. % to about 35 wt. %, or about 15 wt. % to about 32.5 wt. %, or about 15 wt. % to about 30 wt. %, or about 15 wt. % to about 27.5 wt. %, or about 15 wt. % to about 25 wt. %, or about 17.5 wt. % to about 22.5 wt. %, or about 17.5 wt. % to about 32.5 wt. %, or about 20 wt. % to about 30 wt. %, or about 22.5 wt. % to about 27.5 wt. %, or the amount is about 15 wt. %, or about 17.5 wt. %, or about 20 wt. %, or about 22.5 wt. %, or about 25 wt. %, or about 27.5 wt. %, or about 30 wt. %, or about 32.5 wt. %, or about 35 wt. %, or about 37 wt. %, or about 40 wt. %, or about 42.5 wt. %, or about 45 wt. %, all calculated as $Cr_2O_3$ on a calcined basis.

In some embodiments of the dehydrogenation catalysts as otherwise described herein, sodium is present in the dehydrogenation catalyst in an amount within the range of about 0.1 wt. % to about 5 wt. %. In certain embodiments, sodium is present in the dehydrogenation catalyst in an amount within the range of about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or about 0.1 wt. % to about 2 wt. %, e.g., about 0.1 wt. % to about 1.9 wt. %, or about 0.1 wt. % to about 1.8 wt. %, or about 0.1 wt. % to about 1.7 wt. %, or about 0.1 wt. % to about 1.6 wt. %, or about 0.1 wt. % to about 1.5 wt. %, or about 0.1 wt. % to about 1.4 wt. %, or about 0.2 wt. % to about 1.3 wt. %, or about 0.3 wt. % to about 1.2 wt. %, or about 0.4 wt. % to about 1.1 wt. %, or about 0.5 wt. % to about 1 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, calculated as sodium oxide on a calcined basis.

In some embodiments of the dehydrogenation catalysts as otherwise described herein, zirconium oxide is present in the dehydrogenation catalyst in an amount within the range of about 0.1 wt. % to about 5 wt. %, e.g., about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, all calculated as $ZrO_2$ on a calcined basis.

In some embodiments of the dehydrogenation catalysts as otherwise described herein, potassium oxide is present in the dehydrogenation catalyst in an amount within the range of about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or about 0.1 wt. % to about 2 wt. %, e.g., about 0.1 wt. % to about 1.9 wt. %, or about 0.1 wt. % to about 1.8 wt. %, or about 0.1 wt. % to about 1.7 wt. %, or about 0.1 wt. % to about 1.6 wt. %, or about 0.1 wt. % to about 1.5 wt. %, or about 0.1 wt. % to about 1.4 wt. %, or about 0.2 wt. % to about 1.3 wt. %, or about 0.3 wt. % to about 1.2 wt. %, or about 0.4 wt. % to about 1.1 wt. %, or about 0.5 wt. % to about 1 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, calculated as potassium oxide on a calcined basis.

But in other embodiments of the dehydrogenation catalysts as otherwise described herein, potassium is present in the dehydrogenation catalyst in an amount of less than about 0.1 wt. %, e.g., less than about 0.05 wt. %, or less than about 0.02 wt. %, or less than about 0.01 wt. %, calculated as potassium oxide on a calcined basis. In certain embodiments, substantially no potassium oxide is present in the dehydrogenation catalyst.

In some embodiments of the dehydrogenation catalysts as otherwise described herein, magnesium oxide is present in the dehydrogenation catalyst in an amount within the range of about 0.1 wt. % to about 5 wt. %, e.g., about 0.1 wt. % to about 4.75 wt. %, or about 0.1 wt. % to about 4.5 wt. %, or about 0.1 wt. % to about 4.25 wt. %, or about 0.1 wt. % to about 4 wt. %, or about 0.15 wt. % to about 3.75 wt. %, or about 0.2 wt. % to about 3.5 wt. %, or about 0.25 wt. % to about 3.25 wt. %, or about 0.3 wt. % to about 2.75 wt. %, or about 0.35 wt. % to about 2.5 wt. %, or the amount is about 0.1 wt. %, or about 0.15 wt. %, or about 0.2 wt. %, or about 0.25 wt. %, or about 0.3 wt. %, or about 0.35 wt. %, or about 0.4 wt. %, or about 0.45 wt. %, or about 0.5 wt. %, or about 0.55 wt. %, or about 0.6 wt. %, or about 0.7 wt. %, or about 0.8 wt. %, or about 0.9 wt. %, or about 1 wt. %, or about 1.5 wt. %, or about 2 wt. %, or about 2.5 wt. %, or about 3 wt. %, or about 3.5 wt. %, or about 4 wt. %, or about 4.5 wt. %, as MgO on a calcined basis In one particular embodiment of the dehydrogenation catalyst as otherwise described herein, the dehydrogenation catalyst comprises sodium (e.g., substantially as sodium oxide), present in an amount within the range of about 0.1 wt. % to about 5 wt. % (or any other amount detailed above) calculated as sodium oxide on a calcined basis; and zirconium (e.g., substantially as zirconium oxide) present in an amount within the range of about 0.1 wt. % to about 5 wt. % (or any other amount detailed above) calculated as $ZrO_2$ on a calcined basis. In another embodiment, the dehydrogenation catalyst comprises sodium (e.g., substantially as sodium oxide) present in an amount within the range of about 0.1 wt. % to about 5 wt. % (or any other amount detailed above) calculated as sodium oxide on a calcined basis; and potassium (e.g., substantially as potassium oxide) present in an amount within the range of about 0.1 wt. % to about 5 wt. % (or any other amount detailed above) calculated as potassium oxide on a calcined basis. In yet another embodiment, the dehydrogenation catalyst comprises alkali metal (e.g., substantially as alkali metal oxide such as sodium oxide and/or potassium oxide), present in an amount sufficient to provide the catalyst with alkali metal within the range of about 0.1 wt. % to about 5 wt. % (or any other amount detailed above) calculated as alkali metal oxide on a calcined basis; and zirconium present within the range of about 0.1 wt. % to about 5 wt. % (or any other amount detailed above), calculated as $ZrO_2$ on a calcined basis. In yet another embodiment, the dehydrogenation catalyst comprises alkali metal (e.g., substantially as alkali metal oxide such as sodium oxide and/or potassium oxide), present in an amount within the range of about 0.1 wt. % to about 5 wt. % (or any other amount detailed above) calculated as alkali metal oxide on a calcined basis; and magnesium (e.g., substantially as magnesium oxide) present in an amount within the range of about 0.1 wt. % to about 5 wt. % (or any other amount detailed above) calculated as MgO on a calcined basis. In another embodiment, the dehydrogenation catalyst comprises zirconium (e.g., substantially as zirconium oxide) present in an amount within the range of about 0.1 wt. % to about 5 wt. % (or any other amount detailed above), calculated as $ZrO_2$ on a calcined basis; and magnesium (e.g., substantially as magnesium oxide) present in an amount within the range of about 0.1 wt. % to about 5 wt. % (or any other amount detailed above) calculated as MgO on a calcined basis.

Another embodiment of the disclosure is a method of dehydrogenating hydrocarbons. The method includes providing a dehydrogenation catalyst as described herein (e.g., as made by any method as described herein). The method also includes contacting a hydrocarbon feed with the provided dehydrogenation catalyst. In one example, isobutene is converted to isobutylene. In another example, n-butane is converted to n-butenes. In yet another example, propane is converted to propylene. In a typical process, the hydrocarbon feed is fed into a pressure vessel containing the dehydrogenation catalyst of this disclosure. The feed may be introduced into the reactor bed containing the dehydrogenation catalyst at a constant rate, or alternatively, at a variable rate. The feed may be heated to an elevated temperature before introduction to the reactor bed. The catalyst may be contained in one bed within a reactor vessel or divided up among a plurality of beds within a reactor. The dehydrogenation reaction system may contain one or more reaction vessels in series. The feed to the reaction zone can flow vertically upwards, or downwards through the catalyst bed in a typical plug flow reactor, or horizontally across the catalyst bed in a radial flow type reactor. A controlled amount of water, in quantities between about 0.01% and about 6% of the hydrocarbon feed, is preferably added to the reaction zone, in order to prevent dehydration of the catalyst, which can affect catalyst performance In certain embodiments of the methods as described herein, the hydrocarbon feed may include any C3, C4, or C5 hydrocarbon. The hydrocarbons may be straight-chain or branched hydrocarbons, or a mixture thereof. As the person of ordinary skill in the art will appreciate, the hydrocarbon feed may include a number of combinations of C3, C4, and/or C5 hydrocarbons. In some embodiments, the hydrocarbon feed includes propane. In some embodiments, the hydrocarbon feed includes isobutene. In some embodiments, the hydrocarbon feed includes n-butane.

In some embodiments of the methods as described herein, the hydrocarbon is contacted with the provided dehydrogenation catalyst at a liquid hourly space velocity (LHSV) of about 0.25 $h^{-1}$ to about 2 $h^{-1}$, e.g., about 0.25 $h^{-1}$ to about 1.75 $h^{-1}$, or about 0.5 $h^{-1}$ to about 1.5 $h^{-1}$, or about 0.75 $h^{-1}$ to about 1.25 $h^{-1}$, or is about 0.25 $h^{-1}$, or about 0.5 $h^{-1}$, or about 0.75 $h^{-1}$, or about 1 $h^{-1}$, or about 1.25 $h^{-1}$, or about 1.5 $h^{-1}$, or about 1.75 $h^{-1}$, or about 2 $h^{-1}$.

In some embodiments of the methods as described herein, the contacting of the hydrocarbon feed with the catalyst is carried out a temperature within the range of about 300° C. to about 800° C., e.g., about 325° C. to about 800° C., or about 350° C. to about 800° C., e.g., about 375° C. to about 775° C., or about 400° C. to about 750° C., or about 425° C. to about 725° C., or about 450° C. to about 700° C., or about 475° C. to about 675° C., or about 500° C. to about 625° C., or about 525° C. to about 600° C., or the temperature is about 400° C., or about 425° C., or about 450° C., or about 475° C., or about 500° C., or about 525° C., or about 540° C., or about 555° C., or about 570° C., or about 585° C., or about 600° C., or about 625° C., or about 650° C., or about 675° C., or about 700° C.

EXAMPLES

The Examples that follow are illustrative of specific embodiments of the invention, and various uses thereof. They are set forth for explanatory purposes only, and are not to be taken as limiting the invention.

Example 1. Dehydrogenation Catalyst Preparation and Use

Bayerite aluminum hydroxide, ACCROX chromium(III) oxide (Elementis, Stockton-on-Tees, U.K.), nitric acid, polyethylene and water were mixed and pelletized using a mixer-muller. The pelletized mixture was dried at 120° C., then calcined at 600° C.

The calcined material was then impregnated with an aqueous solution containing 37 wt. % chromium nitrate, along with sodium hydroxide, magnesium nitrate and zirconium carbonate. The impregnated material was calcined for at 760° C. The calcined, impregnated material, contained 24.5 wt. % $Cr_2O_3$, 0.6 wt. % $Na_2O$, 1.0 wt. % MgO and 0.7 wt. % $ZrO_2$, with the balance of the material being $Al_2O_3$ The calcined mixture was placed in a reactor and tested for propane dehydrogenation activity at various reactor temperatures, at a liquid hourly space velocity (LHSV) of 1 $h^{-1}$. The test reactions were performed in cyclic dehydrogenation-regeneration mode, at a temperature ranging from 538-593° C. at dehydrogenation pressure 0.5 atm and regeneration pressure 1 atm. The cycle consisted of 3 minutes of reduction of catalyst by $H_2$ at dehydrogenation temperature, followed by dehydrogenation for 10 minutes. After dehydrogenation, the catalyst was regenerated in air for 15 minutes at the dehydrogenation temperature. Table 1 shows the catalytic performance of the carrier in a dehydrogenation reaction (i.e., the calcined material before solution impregnation of chromium, zirconium and sodium) compared to a dehydrogenation catalyst prepared using the conventional impregnation of an alumina carrier by chromic acid (i.e., Cr(VI)).

TABLE 1

Impregnated Propylene Dehydrogenation Catalyst Performance

| Catalyst Properties | Dehydrogenation Catalyst made by Impregnation of aluminum-chromium carrier | Reference Catalyst |
|---|---|---|
| Total $Cr_2O_3$ (wt. %) | 24.5 | 19.6 |
| Activity at 538° C. | | |
| C1 to C2 (wt. %) | 2.43 | 2.47 |
| Propane Conversion (wt. %) | 36.28 | 37.00 |
| Propylene Selectivity (wt. %) | 83.08 | 83.29 |
| Propylene Yield (wt. %) | 30.1 | 30.79 |
| Coke Yield (wt. %) | 1.07 | 0.83 |
| Activity at 567° C. | | |
| C1 to C2 (wt. %) | 4.81 | 5.14 |
| Propane Conversion (wt. %) | 49.45 | 49.52 |
| Propylene Selectivity (wt. %) | 79.23 | 77.74 |
| Propylene Yield (wt. %) | 39.23 | 38.58 |
| Coke Yield (wt. %) | 1.49 | 1.60 |
| Activity at 593° C. | | |
| C1 to C2 (wt. %) | 8.51 | 10.08 |
| Propane Conversion (wt. %) | 62.42 | 62.84 |
| Propylene Selectivity (wt. %) | 72.59 | 68.59 |
| Propylene Yield (wt. %) | 45.25 | 43.01 |
| Coke Yield (wt. %) | 3.66 | 4.47 |

These results demonstrate that the dehydrogenation catalysts of the disclosure, prepared without Cr(VI)-containing materials perform similarly or better than conventional dehydrogenation catalysts prepared with Cr(VI)-containing materials.

What is claimed is:

1. A method for preparing a chromium catalyst, the method comprising
   providing a solid aluminum hydroxide and a solid chromium(III) source selected from chromium(III) oxide, chromium(III) hydroxide, chromium(III) halide, chromium(III) acetate or chromium(III) stearate;
   preparing a formable mixture by directly mixing the solid aluminum hydroxide, the solid chromium(III) source and an acid and, if necessary, sufficient water to make the mixture formable, the formable mixture comprising, on a dry basis,
      the aluminum hydroxide, present in an amount within the range of about 40 wt. % to about 90 wt. %;
      the acid, present in an amount within the range of about 2 wt. % to about 15 wt. %; and
      the chromium(III) source, present in an amount within the range of about 10 wt. % to about 35 wt. %;
   forming the formable mixture via extrusion or tabletting; and
   calcining the formed mixture to provide a calcined mixture comprising $Al_2O_3$ and $Cr_2O_3$ impregnate the calcined mixture with an aqueous impregnation solution comprising a chromium (III) salt; and calcining the impregnated mixture, chromium content being present in a calcined catalyst in an amount in the range of 15-50 wt %, as $Cr_2O_3$ on a calcined basis,
wherein the formable mixture before the calcining step comprises less than 1% chromium(VI) as a molar fraction of total chromium.

2. The method according to claim 1, wherein formable mixture before the calcining step comprises less than 0.5% chromium(VI) as a molar fraction of total chromium.

3. The method according to claim 1, wherein the formable mixture includes the aluminum hydroxide present in an amount within the range of about 60 wt. % to about 90 wt. % on a dry basis.

4. The method according to claim 1, wherein the acid is nitric acid, formic acid or acetic acid.

5. The method according to claim 1, wherein the acid is present in the formable mixture in an amount within the range of about 4 wt. % to about 10 wt. %.

6. The method according to claim 1, wherein the chromium(III) source is chromium(III) oxide or chromium(III) hydroxide.

7. The method according to claim 1, wherein the chromium(III) source is present in the formable mixture in an amount within the range of about 10 wt. % to about 25 wt. % on a dry basis.

8. The method according to claim 1, wherein the formable mixture comprises water in an amount within the range of about 3 wt. % to about 20 wt. % on a wet basis.

9. The method according to claim 1, wherein the formable mixture further comprises a pore forming organic compound in an amount within the range of about 0.1 wt. % to about 5 wt. % on a dry basis.

10. The method according to claim 1, wherein the aluminum hydroxide, the acid and the chromium(III) source make up at least about 80 wt. % of the formable mixture on a dry basis.

11. The method according to claim 1, wherein the formed mixture is calcined at a temperature within the range of about 300° C. to about 900° C.

12. The method according to claim 1, wherein
   the formable mixture includes the aluminum hydroxide present in an amount within the range of about 60 wt. % to about 90 wt. % on a dry basis;
   the acid is present in the formable mixture in an amount within the range of about 4 wt. % to about 10 wt. %;
   the chromium(III) source is present in the formable mixture in an amount within the range of about 3 wt. % to about 25 wt. % on a dry basis; and
   the aluminum hydroxide, the acid and the chromium(III) source make up at least about 95 wt. % of the formable mixture on a dry basis.

13. The method according to claim 1, wherein the materials included in the aqueous impregnation solution comprise less than 1% chromium(VI).

14. The method according to claim 1, wherein the aqueous impregnation solution further comprises one or more of
   a sodium salt, present in an amount sufficient to provide the catalyst with sodium within the range of about 0.1 wt. % to about 5 wt. % calculated as sodium oxide on a calcined basis;
   a potassium salt, present in an amount sufficient to provide the catalyst with sodium within the range of about 0.1 wt. % to about 5 wt. % calculated as potassium oxide on a calcined basis;
   a zirconium salt, present in an amount sufficient to provide the catalyst with sodium within the range of about 0.1 wt. % to about 5 wt. % calculated as $ZrO_2$ on a calcined basis;
   a magnesium salt, present in an amount sufficient to provide the catalyst with sodium within the range of about 0.1 wt. % to about 5 wt. % calculated as MgO on a calcined basis.

15. The method according to claim 1, wherein chromium is present in the calcined catalyst in an amount within the range of about 25 wt. % to about 50 wt. %.

16. The method according to claim 1, wherein the formable mixture before the calcining step comprises less than 0.1% chromium(VI) as a molar fraction of total chromium.

* * * * *